US011434227B2

(12) United States Patent
Sinha et al.

(10) Patent No.: US 11,434,227 B2
(45) Date of Patent: Sep. 6, 2022

(54) BROAD SPECTRUM ANTIBACTERIAL ACTIVITY OF NOVEL BISBENZIMIDAZOLES TARGETING TOPOISOMERASE IA AND THE SYNERGISTIC COMPOSITION OF BISBENZIMIDAZOLE WITH EFFLUX PUMP INHIBITORS AGAINST PATHOGENIC BACTERIA

(71) Applicants: Jawaharlal Nehru University (JNU), New Delhi (IN); Vibha Tandon, New Delhi (IN)

(72) Inventors: Devapriya Sinha, Delhi (IN); Vibha Tandon, New Delhi (IN)

(73) Assignees: Vibha Tandon, New Delhi (IN); Jawaharlal Nehru University, New Delhi (IN)

( * ) Notice: Subject to any disclaimer, the term of this patent is extended or adjusted under 35 U.S.C. 154(b) by 8 days.

(21) Appl. No.: 16/072,018

(22) PCT Filed: Jan. 20, 2017

(86) PCT No.: PCT/IN2017/000013
§ 371 (c)(1),
(2) Date: Jul. 23, 2018

(87) PCT Pub. No.: WO2017/125944
PCT Pub. Date: Jul. 27, 2017

(65) Prior Publication Data
US 2019/0023694 A1 Jan. 24, 2019

(30) Foreign Application Priority Data
Jan. 23, 2016 (IN) .............................. 201611002627

(51) Int. Cl.
*C07D 403/14* (2006.01)
*A61K 31/198* (2006.01)
*A61K 31/4184* (2006.01)
*C07D 235/20* (2006.01)
*A61P 31/06* (2006.01)
*A61K 31/277* (2006.01)
*A61K 45/06* (2006.01)
*A61K 38/00* (2006.01)

(52) U.S. Cl.
CPC .......... *C07D 403/14* (2013.01); *A61K 31/198* (2013.01); *A61K 31/277* (2013.01); *A61K 31/4184* (2013.01); *A61K 45/06* (2013.01); *A61P 31/06* (2018.01); *C07D 235/20* (2013.01); *A61K 38/00* (2013.01); *A61K 2300/00* (2013.01); *Y02A 50/30* (2018.01)

(58) Field of Classification Search
CPC .. C07D 403/14; C07D 235/20; A61K 31/198; A61K 31/4184; A61P 31/04; A61P 31/00; A61P 31/06
See application file for complete search history.

(56) References Cited

U.S. PATENT DOCUMENTS 3,538,097 A * 11/1970 Lammler ............. C07D 235/20
544/370
5,770,617 A 6/1998 LaVoie et al.

FOREIGN PATENT DOCUMENTS

WO 2005/113579 A1 12/2005
WO 2015/042438 A1 3/2015

OTHER PUBLICATIONS

Chen et al. (Mitochondrial membrane potential change induced by Hoechst 33342 in myelogenous leukemia cell line HL-60. Ann Clin Lab Sci. 2004 Autumn;34(4):458-66).*
D'Arezzo et al. ("High-level tolerance to triclosan may play a role in Pseudomonas aeruginosa antibiotic resistance in immunocompromised hosts: evidence from outbreak investigation." BMC research notes 5.1 (2012): 43).*
International Search Report and Written Opinion dated May 24, 2017 for International Application No. PCT/IN2017/000013, entitled "Broad Spectrum Antibacterial Activity of Novel Bisbenzimidazoles Targeting Topoisomerase IA and the Synergistic Composition of Bisbenzimidazole With Efflux Pump Inhibitors Against Pathogenic Bacteria."
Bansal et al., "3,4-Dimethoxyphenyl bis-benzimidazole, a novel DNA topoisomerase inhibitor that preferentially targets *Escherichia coli* topoisomerase I," Journal of Antimicrobial Chemotherapy, vol. 67, pp. 2882-2891, (2012).
Song et al., "Recent Development of Benzimidazole-Containing Antibacterial Agents" Chem. Med. Chem., vol. 11, pp. 646-659, (2016).
Coates, et al., "Novel classes of antibiotics or more of the same?," British Journal of Pharmacology, vol. 163, No. 1, pp. 184-194, (2011).
Blair, et al., "Molecular mechanisms of antibiotic resistance," Nature Reviews Microbiology, vol. 13, bages 42-51, (2015).
Agh-Atabay, et al., "Synthesis and investigation of antimicrobial activity of some bisbenzimidazole-derived chelating agents," European Journal of Medicinal Chemistry, vol. 38, No. 10, pp. 875-881, (Oct. 2003).
Moreira, et al., "Antibacterial activity of head-to-head bis-benzimidazoles," Journal of Antimicrobial Agents, vol. 42, Issue 4, pp. 361-366, (Oct. 2013).
Ranjan et al., "Selective inhibition of bacterial topoisomerase I by alkynyl-bisbenzimidazoles," MedChemComm, vol. 5, Issue 4, pp. 816-825, (2014).

(Continued)

*Primary Examiner* — Shobha Kantamneni
(74) *Attorney, Agent, or Firm* — Hamilton, Brook, Smith & Reynolds, P.C.

(57) ABSTRACT

The present invention relates to potent antibacterial activity of novel bisbenzimidazoles (SP12a and SP12b) against both Gram positive and Gram negative bacteria and a synergistic composition comprising Bisbenzimidazole (HN12b) in combination with Efflux pump inhibitors against most of the pathogenic bacterial strains.

16 Claims, 6 Drawing Sheets

(56) References Cited

OTHER PUBLICATIONS

Nimesh, et al., "Synthesis and Biological Evaluation of Novel Bisbenzimidazoles as *Escherichia coli* Topoisomerase IA Inhibitors and Potential Antibacterial Agents," Journal of Medicinal Chemistry, vol. 57, No. 12, pp. 5238-5257, (2014).

Kumar et al., "Modulation of Bacterial Multidrug Resistance Efflux Pumps of the Major Facilitator Superfamily," International Journal of Bacteriology, vol. 2013, Article ID 204141, 15 pages, (2013).

Notification Concerning Transmittal of International Preliminary Report on Patentability for International Application No. PCT/IN2017/000013, "Broad Spectrum Antibacterial Activity of Novel Bisbenzimidazoles Targeting Topoisomerase IA and the Synergistic Composition of Bisbenzimidazole with Efflux Pump Inhibitors Against Pathogenic Bacteria" dated Aug. 2, 2018.

Sinha, D., et al., "Synergistic efficacy of Bisbenzimidazole and Carbonyl Cyanide 3-Chlorophenylhydrazone combination against MDR bacterial strains", Scientific Reports, 7:44419, 14 pages (2017).

\* cited by examiner

BROAD SPECTRUM ANTIBACTERIAL ACTIVITY OF NOVEL BISBENZIMIDAZOLES TARGETING TOPOISOMERASE IA AND THE SYNERGISTIC COMPOSITION OF BISBENZIMIDAZOLE WITH EFFLUX PUMP INHIBITORS AGAINST PATHOGENIC BACTERIA

This application is the U.S. National Stage of International Application No. PCT/IN2017/000013, filed Jan. 20, 2017, which designates the U.S., published in English, and claims priority under 35 U.S.C. § 119 or 365(c) to Indian Application No. 201611002627, filed Jan. 23, 2016. The entire teachings of the above applications are incorporated herein by reference.

This invention relates to antibacterial activity of novel Bisbenzimidazoles 5-(4-butylpiperazin-1-yl)-2'-(3,4-dimethoxyphenyl)-1H,1'H-2,5'-bibenzo[d]imidazole (SP12a) and 5-(4-butylpiperazin-1-yl)-2'-(4-ethoxyphenyl)-1H,1'H-2,5'-bibenzo[d]imidazole (SP12b) against most of the common pathogenic bacterial strains. Further, the present invention relates to synergistic composition comprising Bisbenzimidazole2'-(4-propyl piperazine-1-yl)-1H, 3'H-2,5'-bibenzimidazole (HN12b) and Efflux pump inhibitors carbonyl cyanide-m-chlorophenyl hydrazone (CCCP) and phenylalanine-arginine-β-naphthylamide (PAβN) against most of the common pathogenic strains which is further verified by in vive mice model.

BACKGROUND OF THE INVENTION

The spread of multi drug resistant (MDR) bacterial strains with significant high evolutionary pressure for the development of resistance is a major clinical threat.[1, 2] To overcome this problem, new approaches are required to combat emerging infections and the global spread of drug-resistant bacterial pathogens. One of the strategy could be the development of antibacterial agent against a new drug target. Bisbenzimidazole derived chelating agents have shown antimicrobial activity.[3] Symmetric bisbenzimidazole (BBZ) conjugates ethoxy, amino and methoxy derivatives displayed potent bacteriostatic activity against Methicillin Resistant *Staphylococcus aureus* (MRSA), Vancomycin Resistant Enterococci (VRE), Streptococci, *Listeria monocytogenes* and Mycobacteria as well.[4] Our group has observed for the first time, bisbenzimidazoles (3,4-Dimethoxyphenyl bisbenzimidazole, DMA) as a specific *Escherichia coli* Topoisomerase IA poison inhibitor over Gyrase, Human Topoisomerase I and Human Topoisomerase II.[5] Later it has been observed that bisbenzimidazoles containing a terminal alkyne, are effective and selective inhibitors of *E. coli* topoisomerase IA over DNA Gyrase and Human topoisomerases I and II, and effectively inhibit bacterial growth.[6] Biochemical assays and computational studies demonstrates Bisbenzimidazoles (HN12b) chelates $Mg^{2+}$ required for the religation of DNA and has been observed to restrain growth of most of the pathogenic *E. coli* strains. HN12b was shown to have improved Topoisomerase Inhibition activity as compared to DMA, and has also shown to have significant in vivo efficacy in septicaemia model and neutropenia thigh infection model in Balb/C mice.[7] In view of above, novel Bisbenzimidazoles SP12a and SP12b were designed and developed and the present invention shows with one more carbon chain incremented potent antibacterial activity against broad spectrum pathogenic bacterial strains was observed. To develop an antibacterial agent, it is necessary to understand the modulation of multidrug efflux system in response to the antibacterial agent and also to study the drug translocation across the membrane. Accordingly, the present invention is also on the effect of bisbenzimidazoles on the efflux system of *E. coli* and observed that activated efflux pumps in bacteria can resist bisbenzimidazoles. The present invention shows bisbenzimidazoles in combination with efflux pump inhibitors like carbonyl cyanide-m-chlorophenyl hydrazone (CCCP) and phenylalanine-arginine-β-naphthylamide (PAβN) could enhance antibacterial activity of bisbenzimidazoles manifold which is further proved in neutropenia thigh model in balb C mice.

SUMMARY OF THE INVENTION

Bisbenzimidazoles (HN12b, SP12a and SP12b) acts as a potent antibacterial agent against diverse Gram positive and Gram negative bacteria. These molecules acts as a potent Topoisomerase IA poison inhibitor which is a novel target and shows significant in vivo efficacy; thus development of these molecules as antibacterial agents has further scope in pharmacological interventions. Biochemical assays and computational studies demonstrates Bisbenzimidazoles (HN12b) chelates $Mg^{2+}$ required for, the religation of DNA and has been observed to restrain growth of most of the pathogenic *E. coli* strains. HN12b was shown to have improved Topoisomerase Inhibition activity as compared to DMA, and has also shown to have, significant in vivo efficacy in septicaemia model and neutropenia thigh infection model in Balb/C mice. In view of above, novel Bisbenzimidazoles SP12a and SP12b were designed and developed and the present invention shows butyl group at the piperzine end as in SP12a and SP12b shows improved antibacterial activity against broad-spectrum pathogenic bacterial strains compared to HN12b which bears a propyl group at the piperzine end.

Accordingly, the present invention includes the novel Bisbenzimidazoles (SP12a and SP12b) acts as a potent antibacterial agent against diverse Gram positive and Gram negative bacteria, which are shown with the structure as below:

| Compounds | R¹ | R² |
|---|---|---|
| SP12a | H₃C(H₂C)₃—N(piperazine)— | 2,3-dimethoxyphenyl (—OCH₃, —OCH₃) |
| SP12b | H₃C(H₂C)₃—N(piperazine)— | 4-ethoxyphenyl (—OC₂H₅) |

The biochemical assay results suggest that these compounds act as a poison inhibitor and inhibit DNA religation by chelating the $Mg^{2+}$ responsible for DNA religation. Both HN12b and SP12a shows significant antibacterial efficacy in neutropenia thigh model and septicaemia model in Balb C mice. Accordingly, in continuation of the present study, we explored the effect of these compounds on the different efflux pumps and porins. It was observed isogenic efflux deleted strains get more sensitised against HN12b, SP12a and SP12b in comparison to wild type strains. Real time PCR result shows efflux genes like acrAB-TolC and emrAB-TolC get activated and porins ompC and ompF get down-regulated when treated with bisbenzimidazoles.

Bisbenzimidazoles including the novel Bisbenzimidazoles shows synergistic effect with Efflux pump inhibitors. HN12b shows synergism with Efflux pump inhibitors. Accordingly, the present invention shows, when HN12b are used in combination with efflux pump inhibitor (CCCP and PAβN) a four to eight fold reduction in MIC was observed against most of the pathogenic bacterial strains. Therefore, the present invention includes a synergistic composition comprising Bisbenzimidazole (HN12b), in combination with Efflux pump inhibitors against most of the pathogenic bacterial strains and also shows the in vivo efficacy of the compounds (HN12b and SP12a). The present invention also shows in vivo efficacy of compound HN12b further improves when given in combination of efflux pump inhibitor (CCCP).

BRIEF DESCRIPTION OF THE FIGURES

FIG. 2. Cleavage Religation Inhibition Assay:
A. DMA increased the DNA cleavage product formed by EcTopo1A by shifting the cleavage-religation equilibrium towards DNA cleavage—Cleavage products from 5'-32P labeled ssDNA (S) were analyzed by electrophoresis in a sequencing gel followed by PhosphorImager analysis. Lane 1: no enzyme. Lane 2: with enzyme. Lanes 3-7: with 0.12, 0.25, 0.5, 1, 2 μM DMA present.

B. Cleavage and Religation assay of E. coli topoisomerase IA with compound HN12b. Lane C (Control): pHOT1 Supercoiled Plasmid DNA; Lane CT (Control Topoisomerase IA): pHOT1 DNA+E. coli Topoisomerase IA simultaneous incubation 30 min at 37° C.; Lane CL (Control Ligand): pHOT1 DNA+ 100 μM (concentration of ligand indicated); Lane (1, 5, 10, 25, 50, 75, 100): pHOT1 DNA+E. coli topoisomerase IA+Ligands in the indicated concentrations (1, 5, 10, 25, 50, 75, 100 μM respectively). These experiments were performed in presence and absence of $Mg^+$.

B. Gene expression Analysis shows acrAB-tolC and emr AB-tolC activation and ompC and ompF down-regulation in HN12b Treated E. coli K12 cells.

DETAILED DESCRIPTION OF THE INVENTION

In the present invention Bisbenzimidazole (HN12b, SP12a and SP12b) are observed to be a potent antibacterial agent against both gram positive and gram negative pathogenic bacterial strains. In the present invention the following human pathogenic strains are used: *Enterococcus* sp. (2105), *Enterococcus* sp. (1121), *Enterococcus* sp. (1365), *Enterococcus* sp. (1150), *Enterococcus* sp. (1367), *Enterococcus* sp. (432), *Staphylococcus* sp. (976), *Staphylococcus* sp. (982), *Staphylococcus* sp. (1016) *Acinetobacter baumannii* (MTCC1920), *Acinetobacter baumannii* (AB387), *Pseudomonas aeruginosa* (MTCC1688), *Klebsiella planticola* (MTCC2272), *Salmonella typhimurium* (MTCC1251), *Shigella flexineri* (MTCC1457) are used as reference strains. Since SP12a and SP12b were observed to be more potent as antibacterial activity as compared to HN12b, we checked their effect on virulent and avirulent strains of *M. tuberculosis* and observed that these compounds were effective against *M. tuberculosis* also. Which strengthen our results to develop these molecules as antibacterial agent.

The present invention includes the novel Bisbenzimidazoles, act as a potent antibacterial agent which are shown as below:

wherein R¹ is

R² is

Novel Bisbenzimidazoles (SP12a and SP12b) acts as a potent antibacterial agent against diverse gram positive and gram negative bacteria, which are shown with the structure as below:

| Compounds | R¹ | R² |
|---|---|---|
| SP12a | H₃C(H₂C)₃—N⟨piperazine⟩N— | 3,4-dimethoxyphenyl (OCH₃, OCH₃) |
| SP12b | H₃C(H₂C)₃—N⟨piperazine⟩N— | 4-ethoxyphenyl (OC₂H₅) |

Further embodiment of the present invention includes that these compounds are observed to target Bacterial topoisomerase IA specifically over gyrase, human topoisomerase I and II. Our previous reports suggest that these compounds act as a poison inhibitor (data shown DMA and HN12b) and inhibit DNA religation by chelating the $Mg^{2+}$ responsible for DNA religation (data shown HN12b). HN12b was observed to have good in vivo efficacy against *E. coli* ATCC 25922 in both Neutropenia thigh model and Septicaemia model. In continuation to above study, we observed SP12a shows significant bacterial load reduction in balb/c mice neutropenia thigh model against both gram negative ATCC25922 and Gram positive S1016 strains.

Figure 1:
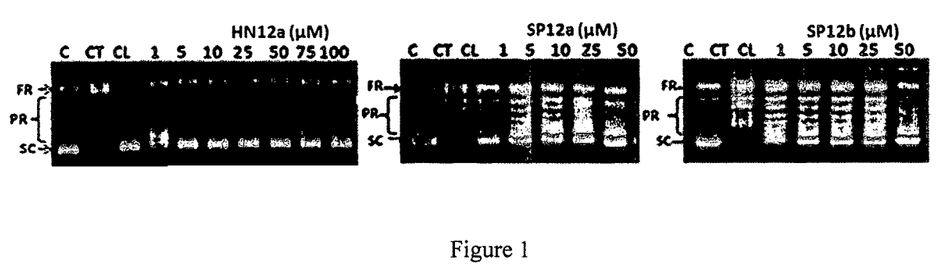
FIG. 1. Relaxation Inhibition Assay:
Inhibition of Relaxation Activity of EcTopo1A in presence of different compounds HN12b, SP12a and SP12b; FR (fully relaxed); PR: (partially relaxed); SC: (super coiled). (A) Ethidium bromide stained agarose gel showing lane 1:pHOT1 plasmid DNA (C), lane 2: relaxation of plasmid DNA by EcTopo1A (CT), lane 3-7: Inhibition of relaxation of plasmid DNA by EcTopo1A in presence of 1, 5, 10, 25 and 50 μM of compounds respectively.
Figure 2:
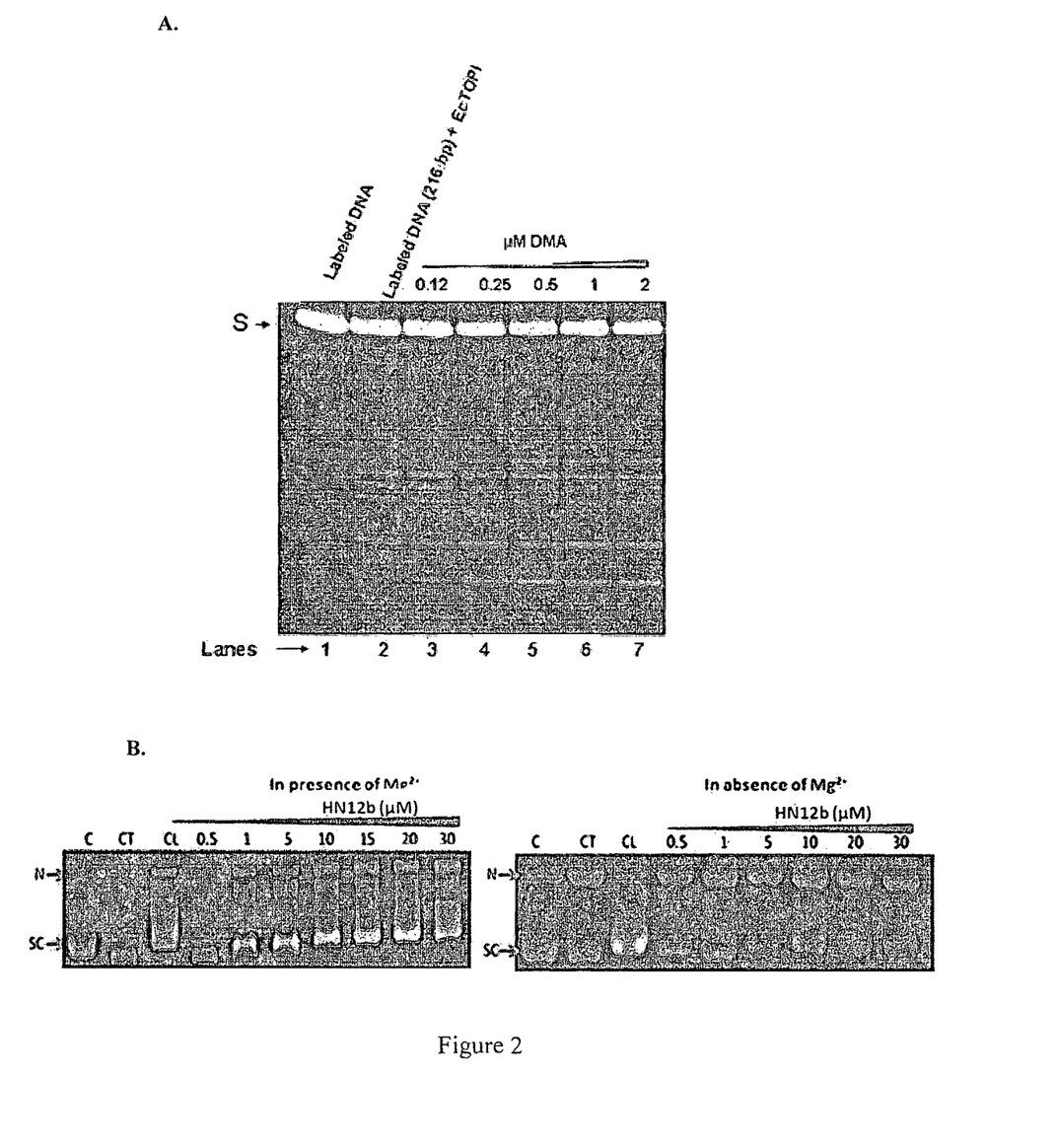
Figure 3:
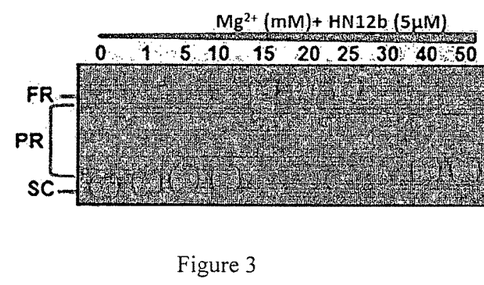
FIG. 3. $Mg^{2+}$ dependent Relaxation Assay:
Ethidium bromide stained agarose gel showing influence of $Mg^{2+}$ concentration on compound HN12b in inhibiting EcTopo 1A. Lane 1-10: Inhibition of relaxation activity EcTopo 1A in presence of 5 μM compound HN12b and 0, 1, 5, 10, 15, 20, 25, 30, 40, 50 mM of $MgCl_2$ respectively.
Figure 4:
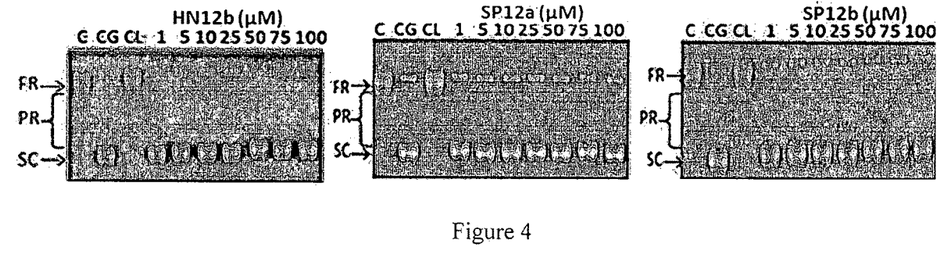
FIG. 4. Gyrase Supercoiling Inhibition Assay:
Analysis of supercoiling of relaxed pHOT I plasmid with E. coli DNA gyrase in the presence of compounds. Ethidium bromide stained agarose gel showing lane 1: pHOT I relaxed plasmid DNA (C), lane 2: supercoiling of relaxed pHOT I plasmid DNA by E. coli DNA gyrase (CG), lane 3: relaxed pHOT I plasmid DNA in presence of compound, lane 4-10: supercoiling inhibition of relaxed pHOT I Plasmid DNA by E. coli DNA gyrase in presence of 1, 5, 10, 25, 50, 75 and 100 μM of compounds respectively.
Figure 5:
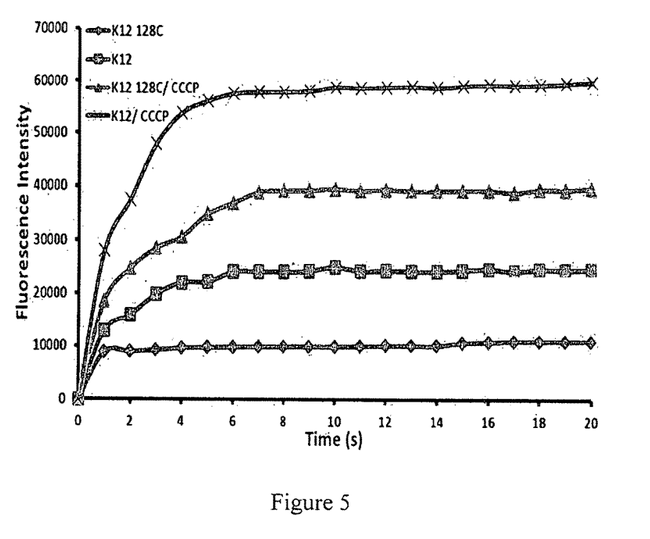
FIG. 5. Effect of Efflux Pump Inhibitor (CCCP) on accumulation HN12b in E. coli K12.
Figure 6:
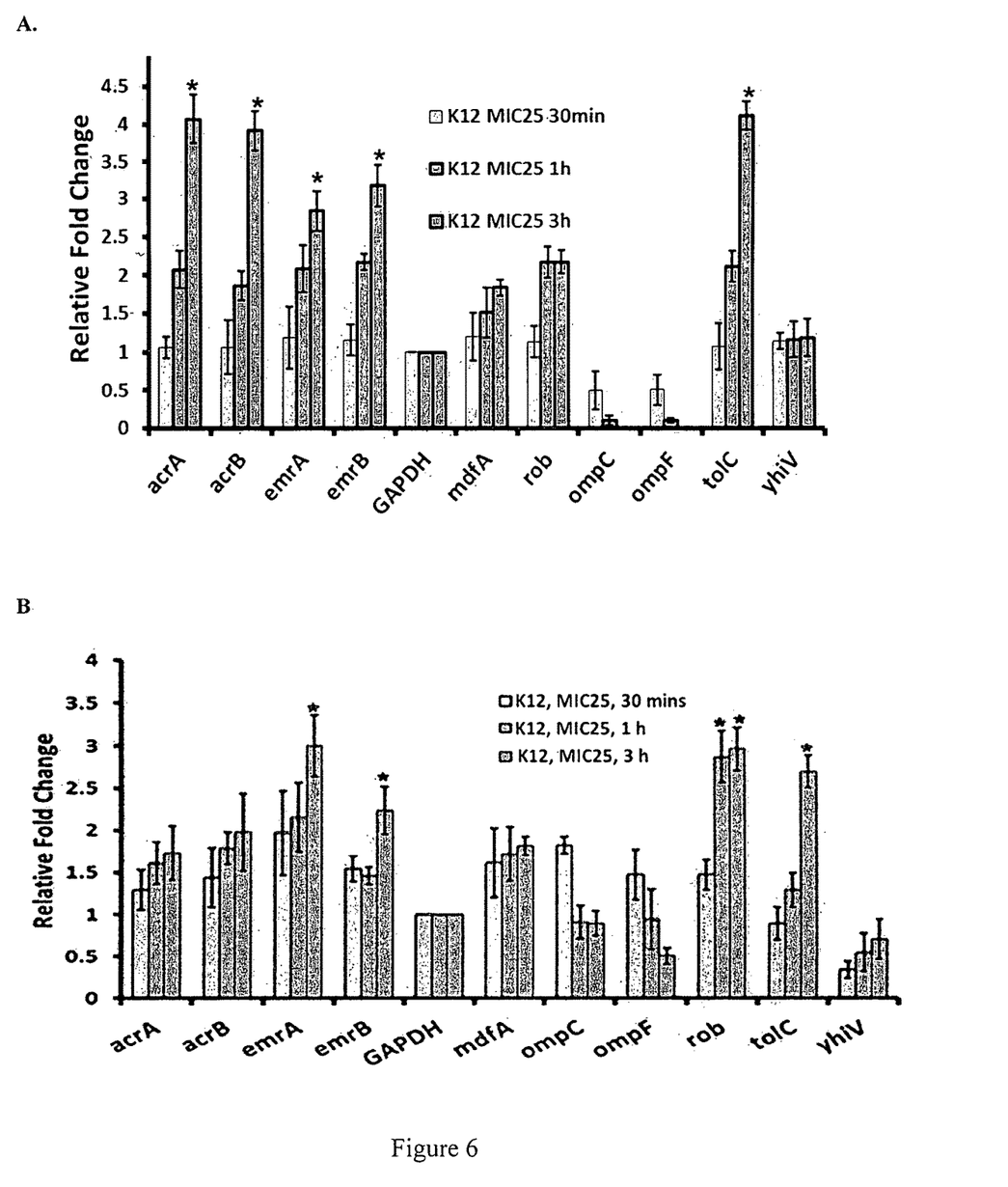
FIG. 6. Gene Expression Analysis:
A. Gene expression Analysis shows acrAB-tolC and emr AB-tolC activation and ompC and ompF down-regulation in Ciprofloxacin Treated E. coli K12 cells.
Figure 7:
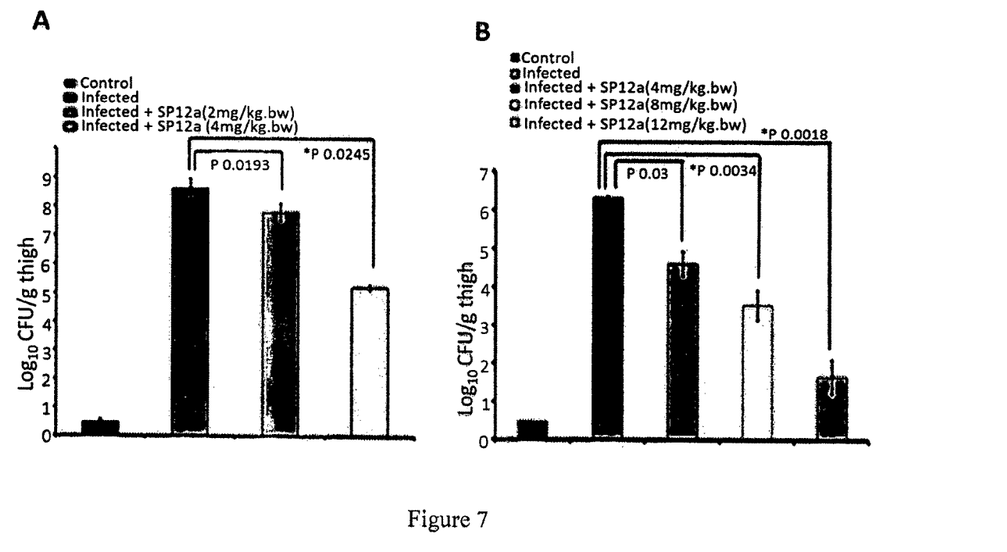
FIG. 7: Efficacy of compound SP12a against E. coli (ATCC25922) and S. aureus (S1016) in Balb/C mice.
A. Efficacy of compound SP12a against ATCC25922 in mouse neutropenic thigh model.
B. Efficacy of compound SP12a against S1016 in mouse neutropenic thigh model. Bar graph showing Log CFU/g Thigh versus drug dose. The standard deviations and errors were calculated.
Figure 8:
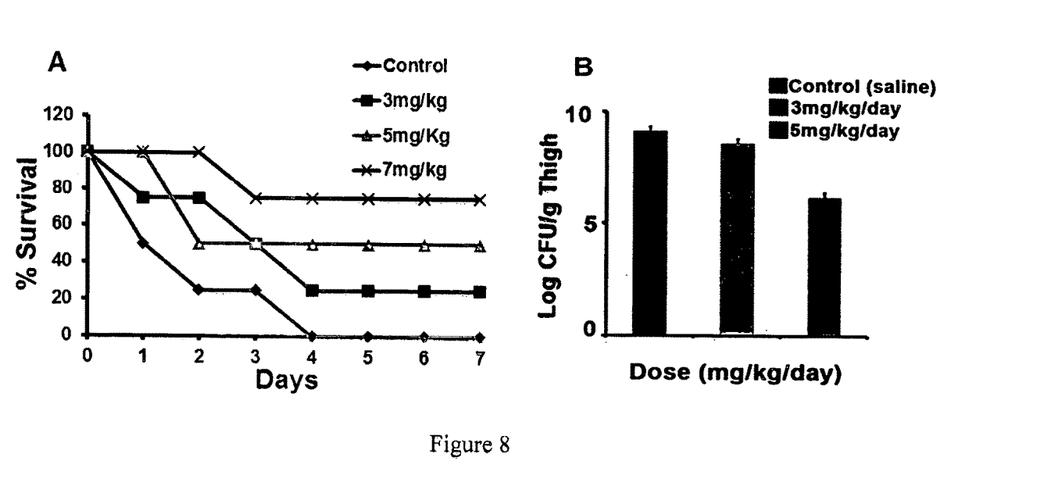
FIG. 8: Efficacy of compound HN12b in mouse infection models.
A. Efficacy of compound HN12b in mouse systemic infection model. Graphical representation of percentage survival versus drug dose (mg/kg body weight).
B. Efficacy of compound HN12b in mouse neutropenic thigh model. Bar graph showing Log CFU/g Thigh versus drug dose. The standard deviations and errors were calculated.

In another embodiment of the present invention the effect of Bisbenzimidazole on the different efflux pumps and porins were studied. It was observed that isogenic efflux deleted strains get more sensitised against HN12b, SP12a and SP12b in comparison to wild type strains. Real time PCR result shows efflux genes like acrAB-TolC and emrAB-TolC get activated and porins like ompC and ompF, get down regulated when treated with bisbenzimidazoles (data shown for HN12b).

Figure 9:
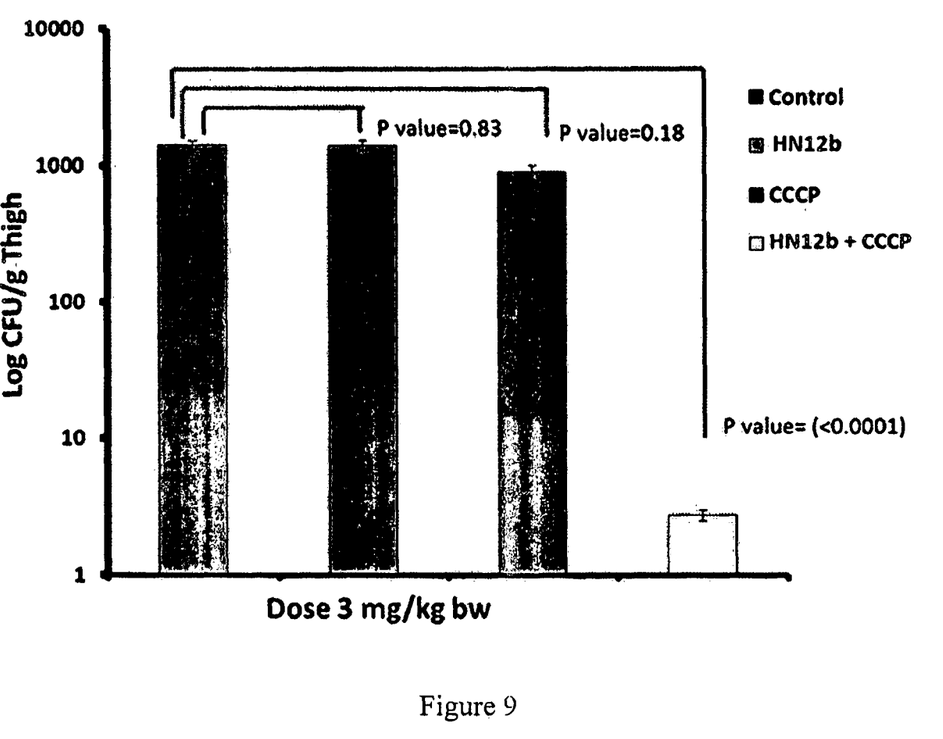
FIG. 9: Efficacy of compound HN12b in combination with CCCP.
Efficacy of compound HN12b in combination with efflux pump inhibitor CCCP in mouse neutropenic thigh model. Bar graph showing Log CFU/g Thigh versus drug dose. The standard deviations and errors were calculated.

The specific embodiment of the present invention shows that when Bisbenzimidazole are used in combination with efflux pump inhibitor (CCCP and PAβN) a four to eight fold reduction in MIC was observed against most of the pathogenic bacterial strains. (data shown for HN12b only), which was further verified through nutropenic thigh model of balbC mice:

In further embodiment of the present invention, an in vivo efficacy of SP12a was studies against both Gram positive (*S. aureus*) and Gram negative (*E. coli*) was studied which shows antibacterial efficacy against both type of bacterial strains.

The most optimized methodology for the present invention is explained in the form of examples below. The present invention is, however, not limited to these examples in any manner. The following examples are intended to illustrate the working of disclosure and not intended to take restrictively to apply any limitations on the scope of the present invention. Those persons skilled in the art will understand that the equivalent substitutes to the specific substances described herein, or the corresponding improvements in the process are considered to be within the scope of this invention.

DETAILED METHODOLOGY AND
EXPERIMENTAL DATA AND RESULTS

Example 1

A. Materials
Bacterial Strains Used:
*Escherichia coli* (ATCC25922) was procured from Himedia ltd, India, *Acinetobacter baumannii* (MTCC1920), *Pseydomonas aeruginosa* (MTCC1688), *Klebsiella planticola* (MTCC2272), *Salmonella typhimurium* (MTCC1251), *Shigella flexineri* (MTCC1457) were procured from CSIR-IMTECH, Chandigarh and *Enterococcus* sp. (MCC2105) was procured from NCCS, Pune. The MDR clinical gram positive strains *Enterococcus* sp. (2105), *Staphylococcus* spp. (1016 and 976) were provided by Dr. Rajni Gaind, Deptt. of Microbiology, Vardhman Mahavir Medical College and Safdarjung Hospital, New Delhi. MDR clinical gram negative strains *Acinetobacter baumannii* (AB387), *Pseudomonas aeruginosa*. (Ps162), *Klebsiella planticola* (K1164), *Salmonella typhimurium* (St412) were obtained from Institute of Pathology, Safdarganj Hospital, New Delhi, a national facility of Govt. of India. ΔompC (CGSC 9781), ΔompF (CGSC 8925), ΔemrA (CGSC 10098), ΔacrA (CGSC 11843), ΔtolC (CGSC 11430), ΔtopA (CGSC8229) and ΔtopB (CGSC 9474), K12 (CGSC 5073) was obtained from *E. coli* Genetic Stock Center (Yale University, USA).

Enzyme and DNA Used:

pHOT1 plasmid DNA was purchased from TopoGen Inc. (Port Orange, Fla., USA). *E. coli* DNA gyrase and its relaxed substrate were purchased from New England Biolabs (GmBH, Germany).

Chemicals Used:

All antibiotics were obtained from Sigma (St Louis, Mo., USA).

Animal Experiments and Ethics:

All animal experiments were approved by Animal ethical committee of Jawaharlal Nehru University, New Delhi, India using ethical guidelines. Animals were maintained under controlled conditions with free access of food and water.

Example 2

A. Methods
Minimal Inhibitory Concentrations Determination

MICs were determined by the broth microdilution method according to CLSI methods (Clinical and Laboratory Standards Institute, 2005). Inoculants were incubated at 37° C. on cation adjusted Mueller Hinton (MH) Broth for 18 to 24 h. Compound were dissolved in media to 10 doubling dilutions from 128 to 0.125 µg/mL. All the bacterial strains were grown in 96 well plate with low evaporation lid (Falcon, Becton Dickinson) in presence of derivatives of benzimidazoles at 0.125, 0.25, 0.5, 1, 2, 4, 8, 16, 32, 64, 128, 256 µg/mL concentrations. Similar experiments were performed with standard antibiotics also. Plates were read by Tecan Micro-plate Reader at 600 nm. $MIC_{50}$ and $MIC_{90}$ value was scored as the minimal concentration that inhibited growth to 50% and 0% at 24 h respectively.

Example 3

Inhibitory Concentration ($IC_{50}$). Determination of Topoisomerase IA by Relaxation Assay

*E. coli* Topoisomerase IA (EcTopoIA) purified protein was diluted in buffer (10 mM Tris-HCl pH 8.0, 50 mM NaCl, 0.1 mg/mL gelatin, 0.5 mM $MgCl_2$). Compounds were added in concentrations 1, 5, 10, 25 and 50 µM to 10 ng of the diluted enzyme present in 20 µL reaction volume. 500 ng of supercoiled pHOT plasmid DNA purified by Qiagen Maxiprep Kit was added. The mixture was incubated at 37° C. for 30 min before termination of the reaction and analysed by agarose gel electrophoresis without Ethidium bromide. The gels were then stained with ethidium bromide which was further photographed over UV transilluminator and analysed by performing densitometry.

Mechanism of inhibition was determined by performing relaxation assay in three different conditions. First, relaxation assay was done with increasing concentrations of $Mg^{2+}$ from 0 to 50 mM to find out optimum concentration of $Mg^{2+}$ required by EcTopo 1A. Second, relaxation assay was performed with increasing concentration of $Mg^{2+}$ in the presence of 5 µM compound and third, reaction we have increased the concentration of compound from 5 to 100 µM in a buffer with 25 mM of $MgCl_2$.

Example 4

Mechanism of Inhibition of Topoisomerase IA by Cleavage and Religation Assay

Compounds at different concentrations were added to DNA cleavage reaction mixtures (20 µl) containing 50 mM TrisHCl, pH 7.5, 2 mM $MgCl_2$ 0.2 mM DTT, 0.5 mM EDTA, 30 µg/ml BSA, 25 µg/ml of pHOT1 having specific site for DNA, 40 units of *E. coli* Topoisomerase IA and ligands was incubated at 37° C. for 30 min. The reactions was then terminated by adding 1% SDS and 150 µg/m Proteinase K, and incubated further for 1 h at 37° C. The DNA samples was electrophoresed in 1% agarose gel in 0.5×TBE. Ethidium bromide at a finial concentration of 0.5 µg/ml was included in the gel to resolve slowly migrating nicked product (cleavable complex) from the supercoiled DNA molecules.

Example 5

Inhibitory Concentration ($IC_{50}$) Determination DNA Gyrase by Supercoiling Inhibition Assay In DNA supercoiling assay, 0.5 µg of relaxed plasmid DNA pHOT1 was incubated with 1 unit of *E. coli* DNA gyrase at 37° C. for 30 min in 25 µL reaction volume containing 1, 5, 10, 25, 50, 75 and 100 µM of compounds. Reactions were terminated by adding 10 mM EDTA, 0.5% SDS, 0.25 µg/mL bromophenol blue, and 15% glycerol and then analysed in agarose gel electrophoresis. The gels were stained after the agarose gel is run with 5 µg/mL ethidium bromide, destained in water and photographed under UV illumination at alpha imager 2200.

Example 6

Inhibitory Concentration ($IC_{50}$) Determination of Human Topoisomerase IB by Relaxation Inhibition Assay DNA topoisomerase I (Human) was assayed by measuring decreased mobility of relaxed isomers of supercoiled plasmid pHOT1 DNA in an agarose gel. Standard topoisomerase assay mixture (25 µl) contained 25 mMTris-HCl (pH 7.5), 5% glycerol, 50 mMKC1, 0.5 mM dithiothreitol (DTT), 30 µg/ml bovine serum albumin (BSA), 0.5 µg supercoiled DNA and, 2 units of enzyme (1 unit is defined as amount of DNA required to convert 50% of 0.5 µg supercoiled DNA substrate into relaxed form under standard assay conditions) in absence and presence of varying drug concentrations. Reactions were performed at 37° C. for 30 min, and then terminated by adding 10 mM EDTA, 0.5% SDS, and 0.25 µg/ml Bromophenol Blue and 15% (v/v) glycerol. Samples were electrophoresed in a horizontal 1% agarose gel in TBE buffer (40 mM Tris/borate, 2 mM EDTA, pH=8.0) at room temperature. Gels were stained with ethidium bromide (0.5 µg/ml), destained in water and photographed under UV illumination at alpha imager 2200.

Example 7

Inhibitory Concentration ($IC_{50}$) Determination of Human Topoisomerase II by Decatenation Assay Reactions were carried out in buffer of 30 mM Tris-HCl, pH 7.6, 3 mM ATP, 15 mM 2-mercaptoethanol, 8 mM $MgCl_2$, 60 mM NaCl in a final volume of 20 µL. Reactions were incubated with 1 unit of enzyme in the presence or absence of the indicated inhibitor for 30 min at 37° C. The reactions were terminated with 2 µL of 10% sodium dodecyl sulfate, followed by proteinase K treatment for 15 min at 37°

C. After addition of 0.1 volume of loading dye (50% glycerol, 0.025% bromophenol blue) samples were extracted once with an equal volume of chloroform: isoamyl alcohol (24:1). Following a brief centrifugation in a microfuge, the blue upper layer was loaded directly onto an agarose gel. The decatenated products were analyzed by electrophoresis in 1% agarose gels with ethidium bromide (0.5 µg/mL) at 100 volts.

Example 8

Real Time Study
RNA Extraction and cDNA Synthesis:
RNA extraction was done by Trizol Method and further purification was done by Qiagen RNA extraction kit. *E. coli* K12 strains were grown in the presence of ¼ MIC HN12b and ¼ MIC Ciprofloxacin for 30 mins, 1 h and 3 h. RNA was extracted from $1 \times 10^7$ cells different. The quality and integrity of the total RNA was assessed using a nanophotometer and agarose gel electrophoresis. After treatment with DNase I (amp grade; Invitrogen), the lack of DNA contamination of the RNA samples was confirmed by polymerase chain reaction (PCR) amplification of rpoB directly from RNA. RNA (1.5 µg) was reverse transcribed according to the manufacturer's recommendations (Accuscript, First Strand cDNA synthesis kit) and the thermal cycling conditions were as follows: 25° C. for 10 min, 42° C. for 60 min, and 85° C. for 5 min. The cDNA was stored at −20° C. Two cDNA preparations were made for each strain.

Quantification of Gene Expression Using Real-Time Quantitative PCR (qPCR):
The assay was performed using a AccuScript High Fidelity RT-PCR Kit. Briefly, each 0.2-mL tube contained 10 µL 2×qPCR mix, 3 pmol each primer, 10 ng cDNA, and RNase-free water to a final volume of 20 µL. The thermal cycling conditions were as follows: 50° C. for 2 min and 95° C. for 8 min, then 45 cycles of denaturation at 94° C. for 10 s, annealing at 59° C. for 15 s, and extension at 72° C. for 20 s, and the last step consisted of a melting curve analysis (65-95° C.). The fold change in the expression of genes under drug stress in the isolates was calculated by 2-ΔΔCT method. GAPDH is a housekeeping gene that is expressed at a stable level in the isolates and can use as an internal invariant control. The expression levels of the 12 genes (acrA, acrB, emrA, emrB, MdfA, GAPDH, tolC, yhiV, rob, ompC and ompF) with and without drug inducement were compared.

Example 9

Fluorescence Study for Efflux and Accumulation Kinetics
Benzimide Accumulation Assay:
Strains were cultured overnight at 37° C. and used to inoculate fresh medium that was incubated for a further 5 h at 37° C. Bacterial cells were collected by centrifugation at 4000 g and resuspended in PBS (1 mL). The optical density of all suspensions was adjusted to 0.1 at 600 nm 17 and aliquots (0.18 mL) were transferred to wells of a 96-well plate (flat-bottomed, black, supplied by Greiner Bio-one, Stonehouse, UK). Four technical replicates of each strain were analysed in each column. The plate was transferred to Infinite® 200 PRO plate reader, incubated at 37° C. and HN12b (20 µM) was added (20 µL) to each well using the autoinjector to give a final concentration of 2 µM. Fluorescence was read from the top of the wells using excitation and emission filters of 355 and 460 nm, respectively, with 5 flashes/well; readings were taken for 30 cycles with a 75 s delay between cycles, and a gain multiplier of 1460. Raw fluorescence values were analysed using Excel (Microsoft) that included calculation of mean values for each column and subtraction of appropriate control blanks. Each experiment was repeated twice. The statistical significance of differences in the accumulation of, HN12b was determined using a paired Student's t-test of each strain compared against appropriate controls such as the parent SL1344. The effect of the inhibitors of efflux, carbonyl cyanide-m-chlorophenyl hydrazone (CCCP) and phenylalanine-arginine-β-naphthylamide (PAβN) was determined by addition immediately before onset of plate reading at timed intervals.

Example 10

Effect of Bisbenzimidazole HN12b in Combination with Efflux Pump Inhibitor 96-well microtiter plates containing $MIC_{25}$ concentrations of the Efflux pump inhibitor (CCCP, PAβN) and HN12b antimicrobial drugs alone and in CB combination were used. The MICs of the individual drugs HN12b, PAβN and CCCP (0.25 to 128 µg/ml) and of the combinations were determined using the broth microdilution technique as recommended by the CLSI. Briefly, the broth microdilution plates were inoculated with each test organism to yield the appropriate density ($10^5$ CFU/ml) in 100 µl Mueller-Hinton broth (MHB) and incubated for 24 h at 37° C. in ambient air. One well with no antibiotic was used as a positive growth control on each plate. Plates were read for visual turbidity, and results were recorded after 24 h of incubation at 37° C. in ambient air by using a magnifying mirror reader, as turbidity in wells indicated growth of the microorganism. The MIC was determined as the well in the microtiter plate with the lowest drug concentration at which there was no visible growth. The MICs of single drugs A and B (MIC A and MIC B) and in combination (MIC AB and MIC BA) were determined after 24 h of incubation at 37° C. in ambient air. MICAB was defined as the MIC of drug A in the presence of drug B; MICBA was defined as the MIC of drug B in the presence of drug A.

Interpretations for CB Method
The fractional inhibitory concentration index (FICI) was calculated for each antibiotic in each combination by using the following formula: FICA+FICB=FICI, where FICA equals the MIC of drug A in combination divided by the MIC of drug A alone and FICB equals the MIC of drug B in combination divided by the MIC of drug B alone. The FICIs were interpreted as follows: FICI of ≤0.5 will correspond to synergy; FICI of >0.5 to ≤1 will correspond to additivity; FICI of >1 to ≤4 will correspond to no interaction (indifference), and FICI of >4 will correspond antagonism.

Example 11

Mouse Systemic Infection Model in Balb C Mice
Female Balb/c mice weighing 20-25 g of 6-8 weeks old were injected with *E. coli* ATCC 25922 ($0.5 \times 10^8$ CFU in 0.1 mL saline) intraperitoneally. At 30 min post inoculation, compound at different doses (3, 5, and 7 mg/kg body weight) dissolved in sterile water as vehicle at a volume of 0.1 mL given single bolus intravenous injection in the tail vein. Each treatment or control group had 10 mice. Mortality was recorded daily for 7 days post infection.

Example 12

Neutropenic Thigh Infection Model in Balb/C Mice

The neutropenic mice thigh infection model, fully described by. Craig, was used in this study. Female Balb/c mice (6 mice per dosing group) weighing 20-25 g were rendered neutropenic with 2 intraperitoneal injections of cyclophosphamide (150 mg/kg of body weight 4 days prior to bacterial inoculation and 100 mg/kg 1 day before inoculation) 2 h prior to bacterial inoculation. This regimen reliably resulted in transient neutropenia in mice that lasted for at least 3 days after the last dose of cyclophosphamide was given. Bacteria were injected into the right thigh of each mouse at time zero. Inocula were selected on the basis of pilot studies with vehicle-treated animals that determined the maximum number of CFU that could be inoculated without substantial, mortality. Neutropenia was defined as an absolute neutrophil count of 500 polymorphonuclear leukocytes/cm$^3$ of blood. The bacterial suspension was diluted to a concentration of $10^6$ CFU/mL with normal saline. Then, 0.1 mL of the bacterial suspension was injected into each posterior thigh muscle 2 h after the second dose of cyclophosphamide was administered. Infected mice were given compound HN12b and SP12a at different doses (2 and 4 mg/kg body weight) dissolved in sterile water as vehicle at a volume of 0.1 mL by single bolus intravenous injection in the tail vein 2 h after bacterial inoculation. Twenty-four hours after drug treatment was begun, the mice were humanely sacrificed. Right thigh muscles from each mouse were aseptically collected, homogenized and serially diluted 1:10 in phosphate buffer saline, and processed for quantitative cultures.

Example 13

Synergistic Effect of CCCP and HN12b in Neutropenic Thigh Infection Model in Balb/C Mice Female Balb/c mice (6 mice per dosing group) weighing 20-25 g were rendered neutropenic with 2 intraperitoneal injections of cyclophosphamide (150 mg/kg of body weight 4 days prior to bacterial inoculation and 100 mg/kg 1 day before inoculation) 2 h prior to bacterial inoculation as described previously. 0.1 mL of the bacterial suspension was injected into right posterior thigh muscle 2 h after the second dose of cyclophosphamide was administered. Infected mice were given compound HN12b (3 mg/kg bw) in combination with CCCP (3 mg/kg bw) dissolved in sterile water as vehicle at a volume of 0.1 mL by single bolus intravenous injection in the tail vein 2 h after bacterial inoculation. Twenty-four hours after drug treatment was begun, the mice were humanely sacrificed. Right thigh muscles from each mouse were aseptically collected, homogenized and serially diluted 1:10 in phosphate buffer saline, and processed for quantitative cultures.

Results

TABLE 1

Susceptibility of Clinical *E. coli* Strains against Bisbenzimidazoles (DMA and HN12b)

| Strain description | DMA | | | HN12b | | |
|---|---|---|---|---|---|---|
| | MIC (mg/L) | PAE (h) | MBC (μM) | MIC$_{50}$ (mg/L) | MIC$_{90}$ (mg/L) | MBC (mg/L) |
| *E. coli* DH5α | 3.74 | 20.8 | 16.0 | 0.2 | 0.2 | 0.8 |
| ATCC 25922 | 14.98 | 22.3 | 64.0 | 0.2 | 3.3 | 4 |
| *E. coli* 72$^R$ | 3.74 | ND | 16.0 | 2 | 3.1 | 4 |
| *E. coli* 118$^R$ | 3.74 | 24 | 16.0 | 1 | 1.7 | 2 |
| *E. coli* 85$^R$ | 3.74 | 24 | 16.0 | 1 | 1.7 | 2 |
| *E. coli* 360$^R$ | 3.74 | 24 | 16.0 | 1 | 1.6 | 2 |
| *E. coli* 451$^R$ | 3.74 | 22 | 16.0 | 1 | 1.7 | 2 |
| *E. coli* 59$^R$ | 7.49 | 1.6 | 32.0 | 2 | 3.4 | 4 |
| *E. coli* 81$^R$ | 7.49 | 23.6 | 32.0 | 1 | 1.6 | 2 |
| *E. coli* 132$^R$ | 7.49 | 24 | 32.0 | 2 | 3.5 | 4 |
| *E. coli* 151$^R$ | 7.49 | 21.6 | 32.0 | 1 | 1.7 | 2 |
| *E. coli* 401$^R$ | 14.98 | 16 | 64.0 | 1 | 1.7 | 2 |
| *E. coli* 555$^R$ | 14.98 | 24 | 64.0 | 4 | 6.8 | 8 |

TABLE 2

Susceptibility of Gram positive/negative Bacterial Strains against Bisbenzimidazoles (HN12b, SP12a and SP12b)

| Strains | HN12b (μg/mL) | | SP12a (μg/mL) | | SP12b (μg/mL) | |
|---|---|---|---|---|---|---|
| | MIC$_{50}$ | MIC$_{90}$ | MIC$_{50}$ | MIC$_{90}$ | MIC$_{50}$ | MIC$_{90}$ |
| | Gram positive | | | | | |
| *Enterococcus* sp. (2105) | 28.4 | 128 | 4.32 | 12.2 | 3.7 | 9.08 |
| *Enterococcus* sp. (1121) | <0.25 | 8 | <0.25 | 0.88 | <0.25 | 0.92 |
| *Enterococcus* sp. (1365) | 0.25 | 11.25 | <0.25 | <0.25 | <0.25 | 2 |
| *Enterococcus* sp.(1150) | 0.25 | 13.25 | <0.25 | <0.25 | <0.25 | 2 |
| *Enterococcus* sp. (1367) | <0.25 | 11.37 | <0.25 | <0.25 | <0.25 | 1 |
| *Enterococcus* sp. (432) | <0.25 | 8.25 | >128 | >128 | >128 | >128 |
| *Staphylococcus* sp. (976) | 0.31 | 15.31 | <0.25 | 0.4 | <0.25 | 0.42 |
| *Staphylococcus* sp. (982) | 0.44 | 7.44 | 0.5 | 1 | >128 | >128 |
| *Staphylococcus* sp. (1016) | 0.57 | 4.57 | 1.2 | 5.7 | <0.25 | 0.92 |
| | Gram negative | | | | | |
| *Escherichia coli* (ATCC 25922) | 8 | 26.6 | 3 | 7.3 | 9.5 | 24.9 |
| *Escherichia coli* 385 | 1.5 | 3.3 | 3.9 | 6.5 | 15 | 27 |
| *Escherichia coli* 392 | 17.9 | 64.5 | 1.5 | 13.7 | 1.8 | 60 |
| *Acinetobacter baumannii* (MTCC1920) | >128 | 128 | 128 | 128 | >128 | 128 |
| *Acinetobacter baumannii* (AB387) | 3.25 | 8 | 3.6 | 10.8 | 12 | 16 |
| *Acinetobacter baumannii* (AB312) | 3.8 | 3.8 | 4.6 | 12.9 | 14.6 | 28.6 |

TABLE 2-continued

Susceptibility of Gram positive/negative Bacterial Strains against Bisbenzimidazoles (HN12b, SP12a and SP12b)

| Strains | HN12b (µg/mL) | | SP12a (µg/mL) | | SP12b (µg/mL) | |
|---|---|---|---|---|---|---|
| | $MIC_{50}$ | $MIC_{90}$ | $MIC_{50}$ | $MIC_{90}$ | $MIC_{50}$ | $MIC_{90}$ |
| *Pseudomonas aeruginosa* (Ps162) | 2.94 | 5.94 | 5.22 | >128 | 40.5 | 70.3 |
| *Pseudomonas aeruginosa* (MTCC1688) | >128 | 128 | 128 | 128 | >128 | 128 |
| *Pseudomonas aeruginosa* (MTCC 366) | 19 | 128 | <0.25 | <0.25 | 0.4 | 0.8 |
| *Klebsiella planticola* (MTCC 2272) | 30.04 | 128 | 128 | 128 | >128 | 128 |
| *Klebsiella planticola* (K1164) | 34.42 | 124 | >128 | 128 | >128 | 128 |
| *Klebsiella planticola* (K235) | 4.52 | 84.52 | 3.1 | 25.9 | 25.9 | 59.5 |
| *Klebsiella planticola* (K589) | 7.4 | 97.4 | 10.3 | 29.4 | 3.4 | 6.8 |
| *Salmonella typhimurium* (MTCC 1251) | <0.25 | <0.25 | <0.25 | 0.25 | <0.25 | 0.25 |
| *Salmonella typhimurium* (St412) | <0.25 | <0.25 | <0.25 | 0.25 | <0.25 | 0.25 |
| *Shigella flexineri* (MTCC1457) | 1.22 | 1.22 | 0.24 | 0.8 | 1.24 | 3.012 |

Antibiotic Resistance Profile:
*A. baumannii* (1920): AMP; TRIM; TET; AB387: CHL, STR, TET; AB312: AMP, KAN, STR, GEN, TRIM;
*K planticola* (MTCC2272): AMP, STR, TRIM, KAN; k1164: AMP, STR, TRIM; k235: TRIM, AMP, KAN, TET, GEN; K589: CHL, TRIM, AMP, CIP, KAN, STR, GEN;
*S. typhimurium* (1251): CIP, AMP, GEN, KAN, TRIM; st412: TET, AMP, CIP, KAN,;
*P. aeruginosa* (MTCC1688): AMP, NAL, KAN TRIM, TET, CHL; Ps162: GEN, KAN, AMP, CIP, TRIM, TET, CHL, Ps 366: TRIM, CHL;
*S. flexineri* (1457): AMP;
*Providencia* sp. (2102): CHL, STR, TET; P592: TRIM, AMP, CIP;
*Enterococcus* sp. (2105): AMP, TET; Ent1121: TRIM, STR, CHL; Ent 1365: AMP, CIP, KAN, STR, TET, GEN; Ent 1150: TET; Ent1367: AMP, KAN; Ent432: AMP, KAN, STR, GEN;
*Staphylococcus* sp. 976: TRIM KAN; ST982: TRIM, KAN, AMP ST1016: KAN, TRIM ABBREVIATIONS:
AMP: Ampicillin,
KAN: Kanamycin,
TRIM: Trimethoprim,
TET: Tetracyclin,
GEN: Gentamycin,
CHL: Chloramphenicol,
NAL: NAlidixic Acid,
CIP: Ciprofloxacin,
STR: Streptomycin.

TABLE 3

Susceptibility of virulent and non-virulent *Mycobacterium tuberculosis* strains against Bisbenzimidazole

| Strains | $MIC_{90}$ (µg/mL) | |
|---|---|---|
| | SP12a | SP12b |
| H37Ra (avirulent) | 7.3 | 1.78 |
| H37Rv (virulent) | 14.59 | 9.8 |

TABLE 4

Susceptibility of Efflux/Influx deprived *E. coli* K12 mutants and Δ TopA and ΔTop B mutants against Bisbenzimidazoles

| Strains | $MIC_{90}$ (µg/mL) | | |
|---|---|---|---|
| | HN12b | SP12a | SP12b |
| *E. coli* K12 | 8 | 16 | 32 |
| ΔacrA | 0.87 | 3.4 | 3.9 |
| ΔemrA | 5.8 | 7.9 | 7.4 |
| ΔtolC | 0.5 | 0.7 | 2.8 |
| ΔompC | 3.8 | 6.7 | 30.9 |
| ΔompF | 5.4 | 6.5 | 30.9 |
| ΔTopIA | 2.8 | 3.9 | 5.7 |
| ΔTopIB | 3.8 | 12.8 | 17.8 |

TABLE 5

FIC Index of Bisbenzimidazole (HN12b) in combination against Efflux Pump Inhibitors (CCCP and PAβN)

| | Strains | HN12b (A) $MIC_{90}$ µg/mL | PAβN (B) $MIC_{90}$ µg/mL | (AB) $MIC_{90}$ µg/mL | (BA) $MIC_{90}$ µg/mL | FICI | Interpretation | CCCP (C) $MIC_{90}$ µg/mL | (AC) $MIC_{90}$ µg/mL | (CA) $MIC_{90}$ µg/mL | FICI | Interpretation |
|---|---|---|---|---|---|---|---|---|---|---|---|---|
| 1 | *E. coli* ATCC25922 | 14 | 64 | 0.3 | 4.8 | 0.1 | Synergy | 11.8 | 1.6 | 2.3 | 0.3 | Synergy |

TABLE 5-continued

FIC Index of Bisbenzimidazole (HN12b) in combination against Efflux Pump Inhibitors (CCCP and PAβN)

| Strains | HN12b (A) MIC$_{90}$ µg/mL | PAβN (B) MIC$_{90}$ µg/mL | (AB) MIC$_{90}$ µg/mL | (BA) MIC$_{90}$ µg/mL | FICI | Interpretation | CCCP (C) MIC$_{90}$ µg/mL | (AC) MIC$_{90}$ µg/mL | (CA) MIC$_{90}$ µg/mL | FICI | Interpretation |
|---|---|---|---|---|---|---|---|---|---|---|---|
| 2 E. coli KK45 | 16 | >128 | 3.1 | 10 | 0.7 | Additive | 12.3 | 4.1 | 1 | 0.3 | Synergy |
| 3 A. baumannii (MTCC1920) | >128 | >128 | 62 | 59 | 0.9 | Additive | 30.2 | 43 | 6.05 | 0.5 | Synergy |
| 4 A. baumannii (AB387) | 8 | >128 | 0.2 | 32 | 0.2 | Synergy | 12 | 0.7 | 1.67 | 0.2 | Synergy |
| 5 K. planticola (MTCC 2272) | >128 | >128 | 59 | 62 | 1 | Additive | 13.9 | 40.9 | 2.9 | 0.5 | Synergy |
| 6 K. planticola (1164) | 128 | >128 | 68 | 62 | 1 | Additive | 14.7 | 42 | 3.3 | 0.5 | Synergy |
| 7 P. aeruginosa (MTCC1688) | >128 | 123 | 63 | 60 | 1 | Additive | 128 | 44 | 38 | 0.6 | Synergy |
| 8 P. aeruginosa (Ps 366) | >128 | 120.2 | 64 | 55 | 0.9 | Additive | 128 | 41 | 39.2 | 0.6 | Synergy |
| 9 Enterococcus sp. (2105) | 128 | >128 | 61 | 59 | 1 | Additive | 27.7 | 36.4 | 6.1 | 0.5 | Synergy |
| 10 Enterococcus sp. (1121) | 8 | >128 | 4.3 | 63 | 1 | Additive | 16.2 | 2.3 | 4.4 | 0.5 | Synergy |
| 11 Providencia sp. (MTCC 2102) | >128 | >128 | 74 | 58 | 1 | Additive | 10.9 | 58 | 2.2 | 0.6 | Additive |
| 12 Providencia sp. (P592) | 58 | >128 | 11 | 38 | 0.4 | Synergy | 67.2 | 20.4 | 20.3 | 0.6 | Additive |

MIC$_{90}$: Minimal Inhibitory Concentration at which 90% of the bacterial survival was inhibited:
AB: MIC$_{50}$ of B/concentration of A
BA: MIC$_{50}$ of A/concentration of B
AC: MIC$_{50}$ of C/concentration of A
CA: MIC$_{50}$ of A/concentration of C
MIC$_{50}$: Minimal Inhibitory Concentration at which 50% of the bacterial survival was inhibited.

TABLE 6

In vivo Efficacy of Compound SP12a

| S. No. | Model | Strain | | SP12a |
|---|---|---|---|---|
| 1 | Neutropenic thigh | ATCC 25922 | MIC$_{90}$ (µg/mL) | 7.3 ± 0.024 |
| | | | Dose at 0.8 log reduction (mg/kg bw/day) | 2 |
| | | | Dose at 3.4 log reduction (mg/kg bw/day) | 4 |
| 2 | Neutropenic thigh | S. aureus 1016 | MIC$_{90}$ (µg/mL) | 5.7 ± 0.046 |
| | | | Dose at 1.7 log reduction (mg/kg bw/day) | 4 |

TABLE 7

In vivo Efficacy of Compound HN12b

| S. No. | Model | Strain | | HN12b |
|---|---|---|---|---|
| 1 | Septicemia | ATCC25922 | MIC$_{50}$(µg/mL) | 0.2 ± 0.024 |
| | | | ED$_{50}$(mg/kg) | 5 |
| 2 | Neutropenic Thigh | | Dose at 1 log reduction (mg/kg/bw/day) | 3 |
| | | | Dose at 3 log reduction (mg/kg/bw/day) | 5 |

REFERENCES

1. (Coates A R, Halls G, Hu Y) British Journal of Pharmacology 2011, 163(1):184-94.
2. (Blair J M, Webber M A, Baylay A J, Ogbolu D O, Piddock L J) Nat Rev Microbiol 2015, 13(1):42-51.
3. (Agh-Atabay N M, Dulger B, Gucin F.) Eur J Med Chem 2003, 38(10):875-81.
4. (Moreira J B, Mann J, Neidle. S, McHugh T D, Taylor P W) Int J Antimicrob Agents 2013, 42(4):361-6.
5. (Bansal S, Sinha D, Singh M, Cheng B, Tse-Dinh Y C, Tandon V) J Antimicrob Chemother 2012, 67(12):2882-91.
6. (Ranjan N, Fulcrand O, King A, Brown J, Jiang X, Leng F, Arya D P) Medchemcomm 2014, 5(6):816-825.
7. (Nimesh H, Sur S, Sinha D, Yadav P, Anand P, Bajaj P, Virdi J S, Tandon V) J Med Chem 2014, 57(12):5238-57.
8. (Kumar S, Mukherjee M M, Varela M F.) Int J Bacteriol 2013, 204141

We claim:

1. A multi-drug resistant bisbenzimidazole antibacterial agent having bacterial topoisomerase IA inhibitory activity and effective against multi-drug resistant pathogens, the antibacterial agent having the structure:

wherein $R^1$ is and R² is wherein the agent is effective against multi-drug resistant pathogens *E. coli, Enterococcus* sp., *Staphylococcus* sp., *Acinetobacter baumannii, Pseudomonas aeruginosa, Klebsiella planticola, Salmonella typhimurium, Shigella flexineri* and *Mycobacterium tuberculosis*.

2. A composition comprising a bisbenzimidazole antibacterial agent and at least one efflux pump inhibitor selected from carbonyl cyanide-m-chlorophenyl hydrazone (CCCP), phenylalanine-arginine-β-naphthylamide (PAβN) or combination of these, wherein the bisbenzimidazole antibacterial agent is selected from the structure:

wherein R¹ and R² are as follows:

| Compounds | R¹ | R² |
|---|---|---|
| SP12a | H₃C(H₂C)₃—N⟨  ⟩N— | —⟨  ⟩—OCH₃ / OCH₃ |
| SP12b | H₃C(H₂C)₃—N⟨  ⟩N— | —⟨  ⟩—OC₂H₅ |

3. The composition of claim 2, wherein the bisbenzimidazole antibacterial agent is present at a concentration of 0.25-128 μg/mL and the at least one efflux pump inhibitor is present at a concentration of 0.25-128 μg/mL.

4. An antibiotic composition comprising a bisbenzimidazole antibacterial agent having bacterial topoisomerase IA inhibitory activity and present in an amount of 0.25-128 μg/mL effective to inhibit the growth of Gram positive or Gram negative bacteria and at least one efflux pump inhibitor present in a concentration of 0.25-128 μg/mL and selected from carbonyl cyanide-m-chlorophenyl hydrazone (CCCP), phenylalanine-arginine-β-naphthylamide (PAβN) or combination of these, wherein the bisbenzimidazole antibacterial agent is selected from the structure:

wherein R¹ and R² are as follows:

| Compound | R¹ | R² |
|---|---|---|
| HN12b | H₃C(H₂C)₃—N⟨  ⟩N— | —⟨  ⟩—OC₂H₅ | wherein the antibacterial agent can selectively inhibit Gram positive or Gram negative bacteria selected from *E. coli, Enterococcus* sp., *Staphylococcus* sp., *Acinetobacter baumanii, Pseudomonas aeruginosa* and *Klebsiella planticola*.

5. The antibiotic composition of claim 4, wherein the bisbenzimidazole antibacterial agent is HN12b and the efflux pump inhibitors are a combination of CCCP and PAβN.

6. A method of inhibiting Gram positive or Gram negative bacteria, comprising contacting a Gram positive or Gram negative bacteria with an effective amount of the composition of claim 2 comprising a bisbenzimidazole antibacterial agent and at least one efflux pump inhibitor, wherein the bacteria is a multi-drug resistant pathogen selected from *E. coli, Enterococcus* sp., *Staphylococcus* sp., *Acinetobacter baumannii, Pseudomonas aeruginosa, Klebsiella planticola, Salmonella typhimurium, Shigella flexineri* or *Mycobacterium tuberculosis*.

7. A method of inhibiting Gram positive or Gram negative bacteria, comprising contacting a Gram positive or Gram negative bacteria with an effective amount of the antibiotic composition of claim 4 comprising a bisbenzimidazole antibacterial agent and at least one efflux pump inhibitor, wherein the Gram positive or Gram negative bacteria is selected from *E. coli, Enterococcus* sp., *Staphylococcus* sp., *Acinetobacter baumanii, Pseudomonas aeruginosa* or *Klebsiella planticola*.

8. The method of claim 7, wherein the bisbenzimidazole antibacterial agent is HN12b and the efflux pump inhibitors are a combination of CCCP and PAβN.

9. The method of claim 6, wherein the composition selectively inhibits bacterial topoisomerase IA but does not inhibit Gyrase, Human Topoisomerase I and Human Topoisomerase II at a concentration of 100 μM.

10. The method of claim 6, wherein the contacting further results in activation of efflux genes acrAB-TolC and emrAB-TolC.

11. The method of claim 6, where the contacting further results in down regulation of porins ompC and ompF.

12. A method of inhibiting Gram positive or Gram negative bacteria comprising contacting a Gram positive or Gram negative bacteria with an effective amount of the multi-drug resistant bisbenzimidazole antibacterial agent of claim 1, wherein the bacteria is a multi-drug resistant pathogen selected from *E. coli, Enterococcus* sp., *Staphylococcus* sp., *Acinetobacter baumannii, Pseudomonas aeruginosa, Klebsiella planticola, Salmonella typhimurium, Shigella flexineri* or *Mycobacterium tuberculosis*.

13. The method of claim 12, wherein the antibacterial agent selectively inhibits bacterial topoisomerase IA but does not inhibit Gyrase, Human Topoisomerase I and Human Topoisomerase II at a concentration of 100 μM.

14. The composition of claim 2, wherein the antibacterial agent and at least one efflux pump inhibitor selectively inhibit bacterial topoisomerase IA in a Gram positive or Gram negative bacteria but does not inhibit Gyrase, Human Topoisomerase I and Human Topoisomerase II at a concentration of 100 μM.

15. The composition of claim 2, wherein the antibacterial agent and at least one efflux pump inhibitor selectively inhibit Gram positive or Gram negative bacteria are selected from *E. coli, Enterococcus* sp., *Staphylococcus* sp., *Acinetobacter baumanii* and *Mycobacterium tuberculosis*.

16. The multi-drug resistant bisbenzimidazole antibacterial agent of claim 1, wherein the antibacterial agent has bacterial topoisomerase IA inhibitory activity in a Gram positive or Gram negative bacteria but does not inhibit Gyrase, Human Topoisomerase I and Human Topoisomerase II at a concentration of 100 µM.

* * * * *